(12) United States Patent
Williams et al.

(10) Patent No.: US 10,568,574 B2
(45) Date of Patent: Feb. 25, 2020

(54) ELECTRODE DEVICE FOR MONITORING AND/OR STIMULATING ACTIVITY IN A SUBJECT

(71) Applicant: THE BIONICS INSTITUTE OF AUSTRALIA, East Melbourne, Victoria (AU)

(72) Inventors: Christopher Edward Williams, East Melbourne (AU); Mark James Cook, East Melbourne (AU); Owen Burns, East Melbourne (AU); Chua Vanessa Maxim, East Melbourne (AU); Alan Lai, East Melbourne (AU)

(73) Assignee: THE BIONICS INSTITUTE OF AUSTRALIA, East Melbourne (AU)

( * ) Notice: Subject to any disclaimer, the term of this patent is extended or adjusted under 35 U.S.C. 154(b) by 0 days.

(21) Appl. No.: 16/124,148

(22) Filed: Sep. 6, 2018

(65) Prior Publication Data
US 2019/0008403 A1 Jan. 10, 2019

Related U.S. Application Data

(63) Continuation of application No. PCT/AU2017/050939, filed on Sep. 1, 2017.

(30) Foreign Application Priority Data

Sep. 1, 2016 (AU) .................................. 2016903501

(51) Int. Cl.
*A61B 5/00* (2006.01)
*A61N 1/05* (2006.01)
(Continued)

(52) U.S. Cl.
CPC ........ *A61B 5/6846* (2013.01); *A61B 5/04001* (2013.01); *A61B 5/04012* (2013.01);
(Continued)

(58) Field of Classification Search
CPC .... A61N 1/0529; A61N 1/37514; A61N 1/05; A61N 1/0504; A61N 1/0553;
(Continued)

(56) References Cited

U.S. PATENT DOCUMENTS 5,231,996 A 8/1993 Bardy et al.
6,030,382 A 2/2000 Fleischman et al.
(Continued)

FOREIGN PATENT DOCUMENTS

WO WO-2009/137234 A2 11/2009
WO WO-2012/038378 A1 3/2012
(Continued)

OTHER PUBLICATIONS

International Application No. PCT/AU2017/050939, International Search Report and Written Opinion, dated Dec. 19, 2017.
(Continued)

*Primary Examiner* — Eun Hwa Kim
*Assistant Examiner* — Catherine Premraj
(74) *Attorney, Agent, or Firm* — Marshall, Gerstein & Borun LLP

(57) ABSTRACT

An electrode device is disclosed comprising: an elongate, implantable body comprising elastomeric material, a plurality of electrodes positioned along a length of the implantable body; an electrical connection comprising one or more conductive elements extending through the elastomeric material and electrically connecting to the electrodes; and a reinforcement device extending through the elastomeric material. The length of the implantable body is extendible by placing the implantable body under tension. The reinforcement device limits the degree by which the length of the implantable body can extend under tension. At least one of the electrodes can extend circumferentially around a portion
(Continued)

of the implantable body. A delivery device and method of delivery for an electrode device is also disclosed.

20 Claims, 13 Drawing Sheets

(51) Int. Cl.
*A61N 1/36* (2006.01)
*A61N 1/375* (2006.01)
*A61B 5/04* (2006.01)
*A61B 5/0476* (2006.01)

(52) U.S. Cl.
CPC .......... *A61B 5/0476* (2013.01); *A61B 5/4094* (2013.01); *A61B 5/6868* (2013.01); *A61B 5/6882* (2013.01); *A61N 1/05* (2013.01); *A61N 1/0504* (2013.01); *A61N 1/0529* (2013.01); *A61N 1/0553* (2013.01); *A61N 1/0558* (2013.01); *A61N 1/36057* (2013.01); *A61N 1/37514* (2017.08); *A61B 2562/0209* (2013.01); *A61B 2562/043* (2013.01); *A61N 1/36064* (2013.01)

(58) Field of Classification Search
CPC .............. A61N 1/0558; A61N 1/36057; A61N 1/36064; A61B 5/04001; A61B 5/05012; A61B 5/0576; A61B 5/4094; A61B 5/6868; A61B 5/6882; A61B 2656/0209; A61B 2656/043
See application file for complete search history.

(56) References Cited

U.S. PATENT DOCUMENTS

| | | | |
|---|---|---|---|
| 7,089,059 B1 | 8/2006 | Pless | |
| 7,209,787 B2 | 4/2007 | DiLorenzo | |
| 8,583,243 B2 | 11/2013 | Williams et al. | |
| 9,517,345 B2 | 12/2016 | Meffin et al. | |
| 2002/0099430 A1* | 7/2002 | Verness | A61N 1/056 607/122 |
| 2002/0128700 A1* | 9/2002 | Cross, Jr. | A61N 1/0529 607/117 |
| 2003/0004428 A1 | 1/2003 | Pless et al. | |
| 2003/0073917 A1 | 4/2003 | Echauz et al. | |
| 2004/0068199 A1 | 4/2004 | Echauz et al. | |
| 2004/0138711 A1 | 7/2004 | Osorio et al. | |
| 2005/0021103 A1* | 1/2005 | DiLorenzo | A61N 1/3605 607/45 |
| 2006/0089691 A1* | 4/2006 | Kaplan | A61N 1/056 607/116 |
| 2007/0225674 A1 | 9/2007 | Molnar et al. | |
| 2007/0249955 A1 | 10/2007 | Carlson et al. | |
| 2007/0265544 A1 | 11/2007 | Carlson et al. | |
| 2008/0021514 A1 | 1/2008 | Pless | |
| 2008/0195166 A1 | 8/2008 | Sun et al. | |
| 2008/0269631 A1 | 10/2008 | Denison et al. | |
| 2010/0100153 A1 | 4/2010 | Carlson et al. | |
| 2010/0106211 A1 | 4/2010 | Lee et al. | |
| 2010/0137928 A1 | 6/2010 | Duncan et al. | |
| 2010/0317955 A1 | 12/2010 | Madsen et al. | |
| 2011/0137371 A1 | 6/2011 | Giftakis et al. | |
| 2012/0095524 A1 | 4/2012 | Nelson et al. | |
| 2012/0203079 A1 | 8/2012 | McLaughlin | |
| 2012/0271386 A1* | 10/2012 | Li | A61N 1/05 607/116 |
| 2012/0277618 A1 | 11/2012 | Giftakis et al. | |
| 2015/0246232 A1 | 9/2015 | Kameneva et al. | |
| 2015/0251002 A1 | 9/2015 | Williams et al. | |
| 2016/0296759 A1 | 10/2016 | Cong et al. | |

FOREIGN PATENT DOCUMENTS

| | | |
|---|---|---|
| WO | WO-2012/058547 A1 | 5/2012 |
| WO | WO-2012/065215 A1 | 5/2012 |
| WO | WO-2015/070252 A1 | 5/2015 |
| WO | WO-2016/038599 A1 | 3/2016 |
| WO | WO-18032060 A1 | 2/2018 |

OTHER PUBLICATIONS

European Patent Application No. 17844694, Supplementary European Search Report, dated Sep. 11, 2019.

* cited by examiner

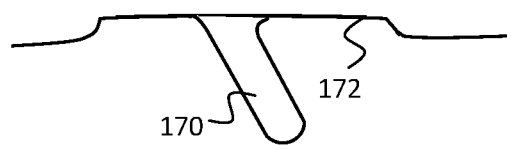
Fig. 7a
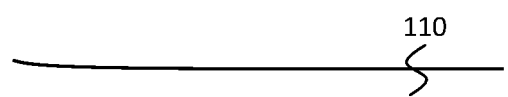
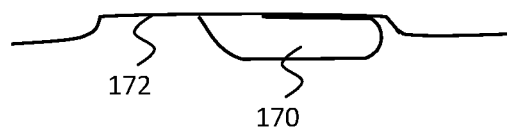
Fig. 7b
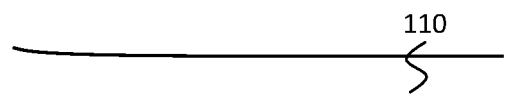
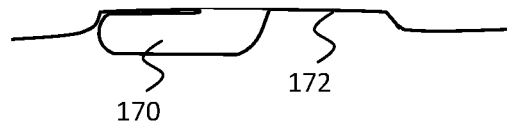
Fig. 7c

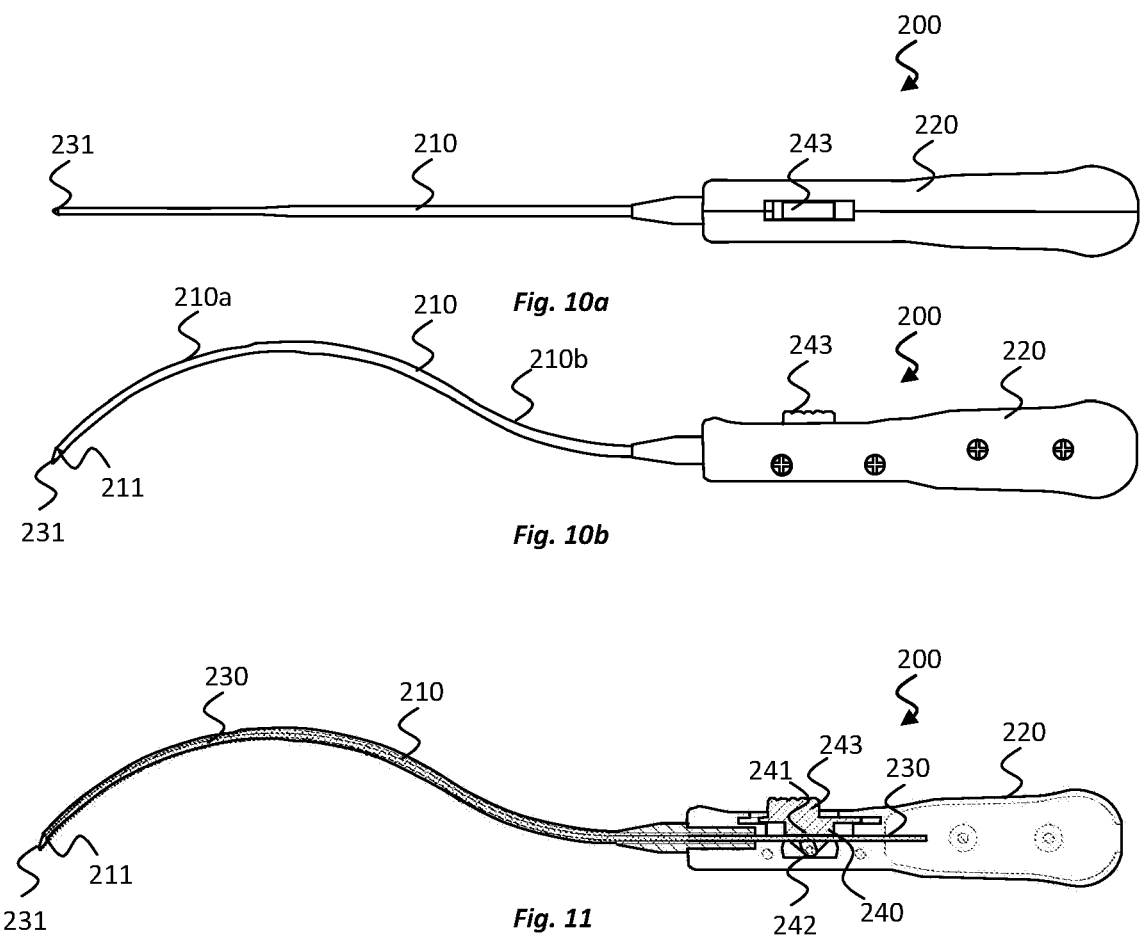

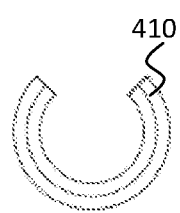
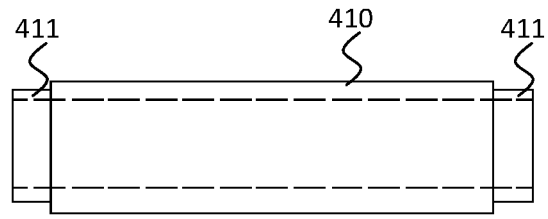
*Fig. 16a*  *Fig. 16b*
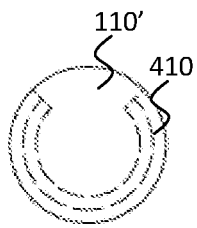
*Fig. 16c*
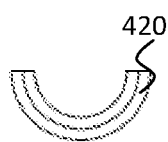
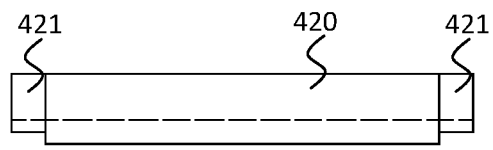
*Fig. 17a*  *Fig. 17b*
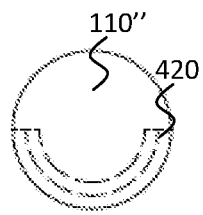
*Fig. 17c*

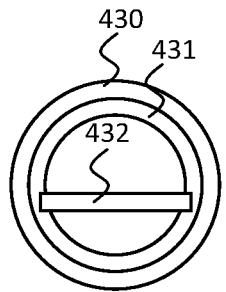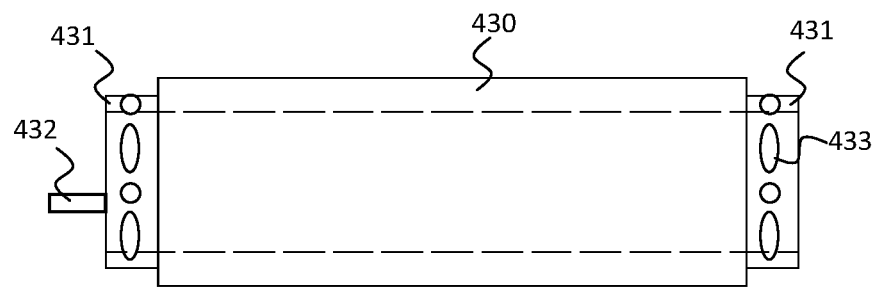
*Fig. 18a*  *Fig. 18b*
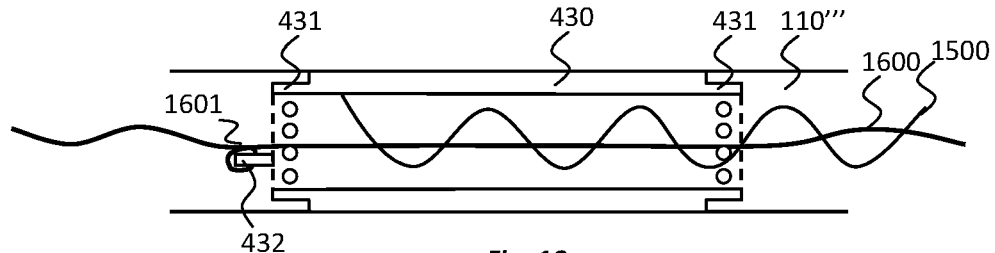
*Fig. 18c*
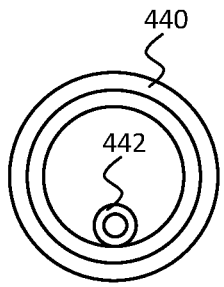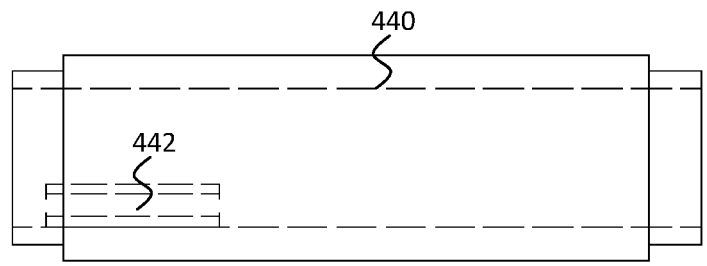
*Fig. 19a*  *Fig. 19b*
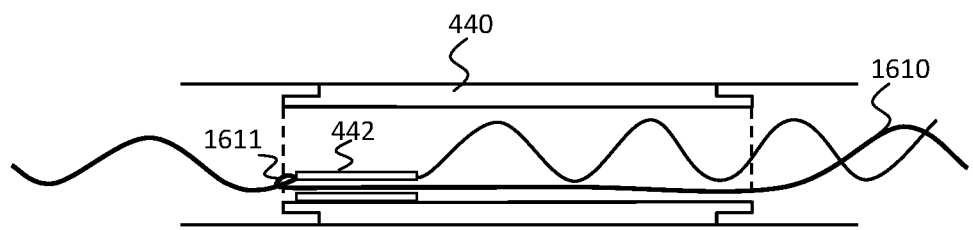
*Fig. 19c*

ELECTRODE DEVICE FOR MONITORING AND/OR STIMULATING ACTIVITY IN A SUBJECT

CROSS-REFERENCE TO RELATED APPLICATIONS

The present application claims priority to Australian Provisional Application No. 2016903501 filed on 1 Sep. 2016, the content of which is herein incorporated by reference.

TECHNICAL FIELD

The present disclosure relates to electrode devices to monitor and/or stimulate activity in a subject, including electrode devices for monitoring brain activity such as epileptic events.

BACKGROUND

Epilepsy is considered the world's most common serious brain disorder, with an estimated 50 million sufferers worldwide and 2.4 million new cases occurring each year.

Epilepsy is a condition of the brain characterized by epileptic seizures that vary from brief and barely detectable seizures to more conspicuous seizures in which a sufferer vigorously shakes. Epileptic seizures are unprovoked, recurrent and due to unexplained causes.

It is desirable to have a safe, reliable and comfortable method of detecting the occurrence of epileptic seizures to enable monitoring of seizure frequency and severity with a view to diagnosing epilepsy and/or determining appropriate seizure control strategies.

Current techniques for monitoring epileptic seizures rely on EEG recordings, typically performed using EEG electrodes attached to the outer surface of the scalp or via surgically implanted intracranial EEG electrodes.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In one aspect, the present disclosure provides an electrode device comprising:
an elongate, implantable body comprising elastomeric material,
a plurality of electrodes positioned along a length of the implantable body;
an electrical connection comprising one or more conductive elements extending through the elastomeric material and electrically connecting to the electrodes; and
a reinforcement device extending through the elastomeric material;
wherein the length of the implantable body is extendible by placing the implantable body under tension, the reinforcement device limiting the degree by which the length of the implantable body can extend under tension.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In another aspect, the present disclosure provides an electrode device comprising:
an elongate, implantable body comprising elastomeric material; and
a plurality of electrodes positioned along a length of the implantable body; and
an electrical connection comprising one or more conductive wires extending through the elastomeric material and electrically connecting to the electrodes;
wherein at least one of the electrodes extends circumferentially around a portion of the implantable body.

In another aspect, the present disclosure provides a delivery device for delivering an electrode device to an implantation location between tissue layers of a subject, the delivery device comprising:
a cannula;
a handle connected to a proximal end of the cannula; and
an inner member that extends at least partially through the cannula and has a distal tip that is exposed at a distal end opening of the cannula, the inner member being removable to provide an opening in the cannula for receiving the electrode device.

In another aspect, the present disclosure provides a method of implanting an electrode device, the method comprising:
forming a first incision and a second incision in tissue of a subject, the first and second incisions being spaced apart;
introducing a cannula through the first incision and pushing the cannula between layers of tissue to the second incision such that the cannula extends between the first and second incisions and at least a distal end opening of the cannula is exposed through the second incision, wherein an inner member extends at least partially through the cannula and has a distal tip that is exposed at the distal end opening of the cannula;
removing the inner member from the cannula via the exposed distal end opening of the cannula;
inserting an electrode device into the cannula; and
withdrawing the cannula from the first incision while leaving the electrode device in a position between the first and second incisions.

These and other aspects of the present disclosure will become apparent to those skilled in the art after a reading of the following detailed description of the invention, including the Figures and appended claims.

BRIEF DESCRIPTION OF DRAWINGS

Embodiments of the present disclosure will not be described by way of non-limiting examples with reference to the following Figures in which:

FIGS. 7a to 7c shows top views of a portion of the electrode device of FIGS. 1a and 1b that includes an anchor;

FIGS. 10a and 10b show top and side views, respectively, of a delivery device for implanting an electrode device according to an embodiment of the present disclosure;

FIG. 11 shows a cross-sectional side view of the delivery device of FIGS. 10a and 10b;

FIGS. 16a and 16b show end and side views, respectively, of an electrode for use in an electrode device according to another embodiment of the present disclosure and FIG. 16c shows an end view of the electrode engaged with an implantable body of the electrode device;

FIGS. 17a and 17b show end and side views, respectively, of an electrode for use in an electrode device according to yet another embodiment of the present disclosure and FIG. 17c shows an end view of the electrode engaged with an implantable body of the electrode device;

FIGS. 18a and 18b show end and side views, respectively, of an electrode for use in an electrode device according to yet another embodiment of the present disclosure and FIG. 18c shows a cross-sectional side view of the electrode engaged with an implantable body of the electrode device; and FIGS. 19a and 19b show end and side views, respectively, of an electrode for use in an electrode device according to yet another embodiment of the present disclosure and FIG. 19c shows a cross-sectional side view of the electrode engaged with an implantable body of the electrode device.

DESCRIPTION OF EMBODIMENTS

Embodiments of the present disclosure relate to the monitoring and/or stimulation of electrical activity in body tissue of a subject using an electrode device comprising a plurality of electrodes, one or more of which electrodes are implanted in the subject. Certain embodiments relate, for example, to electrode devices that are implanted in a head of a subject to monitor brain activity such as epileptic brain activity. However, electrode devices according to the present disclosure may be for implanting in a variety of different locations of the body where monitoring and/or stimulation of electrical activity is desired, including in or on one or more parts of the human or animal digestive system, respiratory system, urinary system, reproductive system, encrodine system, cardivacular system, lymphatic system, integumentary system and the nervous system.

Figure 1A:
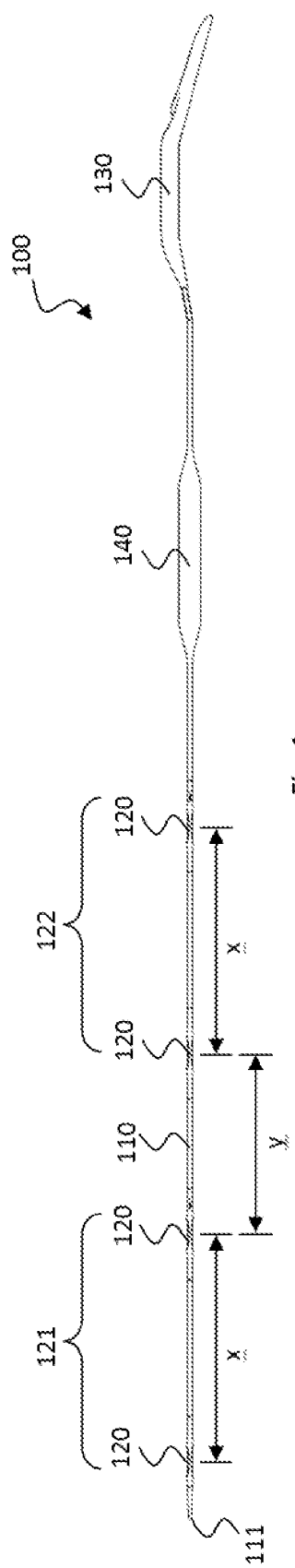
FIGS. 1a and 1b shows side and top views, respectively, of an electrode device according to an embodiment of the present disclosure.
Figure 1B:
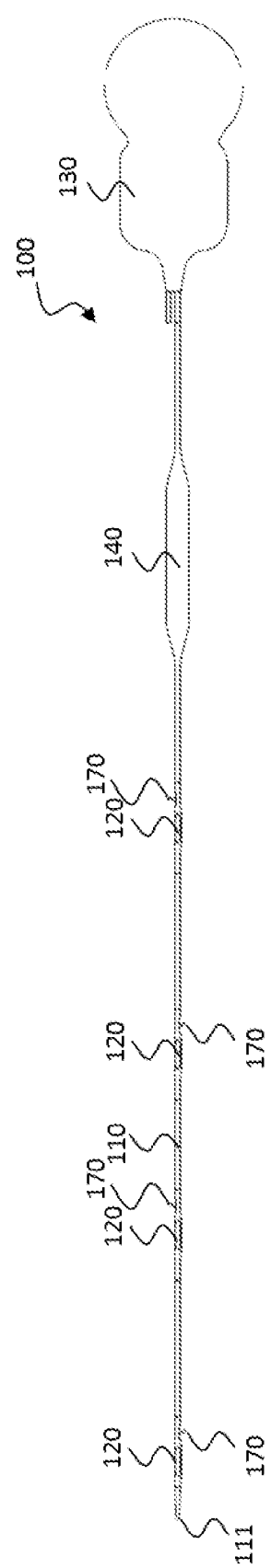
Figure 15A:
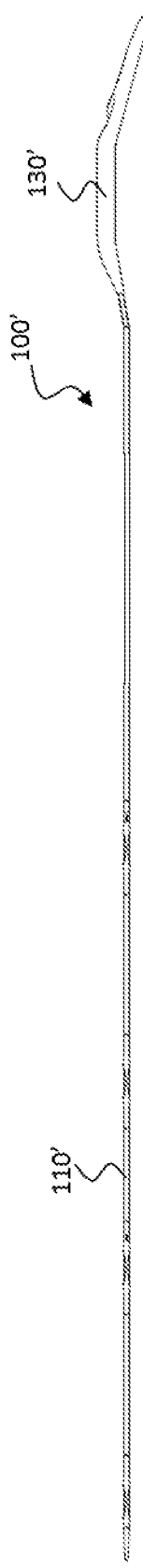
FIGS. 15a and 15b show side and top views, respectively, of an electrode device according to another embodiment of the present disclosure.
Figure 15B:
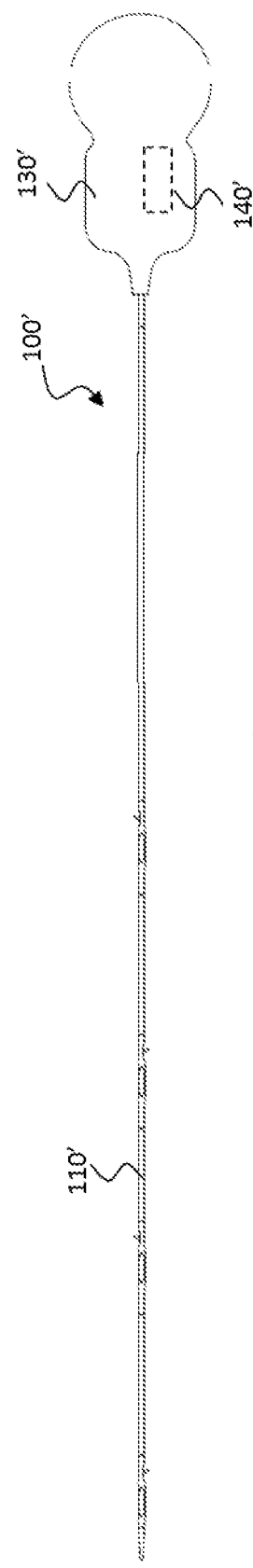

With reference to FIGS. 1a and 1b, in one embodiment an electrode device 100 is provided comprising an elongate, implantable body 110 and a plurality of electrodes 120 positioned along the implantable body 110 in the length direction of the implantable body 110. At a proximal end of the implantable body, a processing unit 130 is provided for processing electrical signals that can be sent to and/or received from the electrodes 120. An electrical amplifier 140 (e.g., a pre-amp) is positioned in the implantable body 110 between the electrodes 120 and the processing unit 130. In an alternative embodiment, as illustrated in FIGS. 15a and 15b, the electrical amplifier 140' may be integrated into the processing unit 130' of the electrode device 100', instead of being positioned in the implantable body 110'.

Figure 3A:
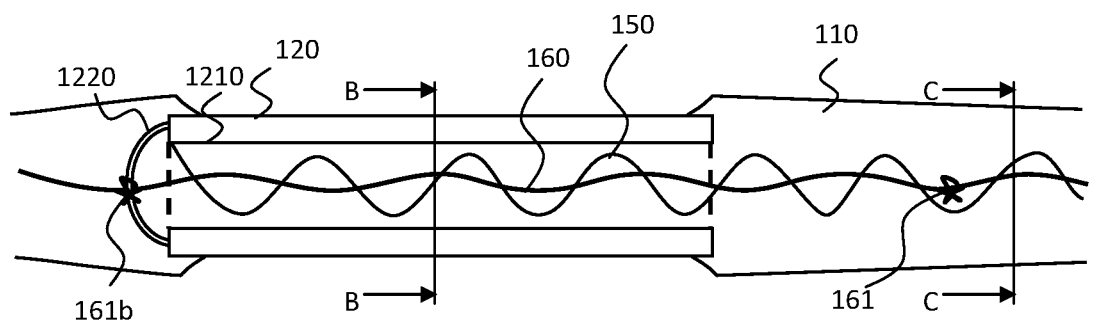
FIGS. 3a to 3c show cross-sectional views of portions of the electrode device of FIGS. 1a and 1b.

With reference to FIG. 3a, which shows a cross-section of a portion of the electrode device 100 adjacent one of the electrodes 120, the electrodes 120 are electrically connected, e.g., to the amplifier 140 and processing unit 130, by an electrical connection 150 that extends through the implantable body 110. A reinforcement device 160 is also provided in the electrode device 100, which reinforcement device 160 extends through the implantable body 110 and limits the degree by which the length of the implantable body 110 can extend under tension.

In this embodiment, referring to FIGS. 1a and 1b, four electrodes 120 are provided that are spaced along the implantable body 110 between the amplifier 140 and a distal tip 111 of the implantable body 110. The distal tip 111 of the implantable body 110 is tapered. The four electrodes 120 are configured into two electrical pairs 121, 122 of electrodes, the two most distal electrodes 120 providing a first pair of electrodes 121 and the two most proximal electrodes 120 providing a second pair of electrodes 122. In this embodiment, the electrodes 120 of the first pair 121 are spaced from each other at a distance x of about 40 to 60 mm, e.g., about 50 mm (measured from centre-to-centre of the electrodes 120) and the electrodes 120 of the second pair 122 are also spaced from each other at a distance x of about 40 to 60 mm, e.g., about 50 mm (measured from centre-to-centre of the electrodes 120). The first and second electrode pairs 121, 122 are spaced from each other at a distance y of about 30 to 50 mm, e.g., about 40 mm (measured from centre-to-centre of the electrodes of the two pairs that are adjacent each other).

Figure 2:
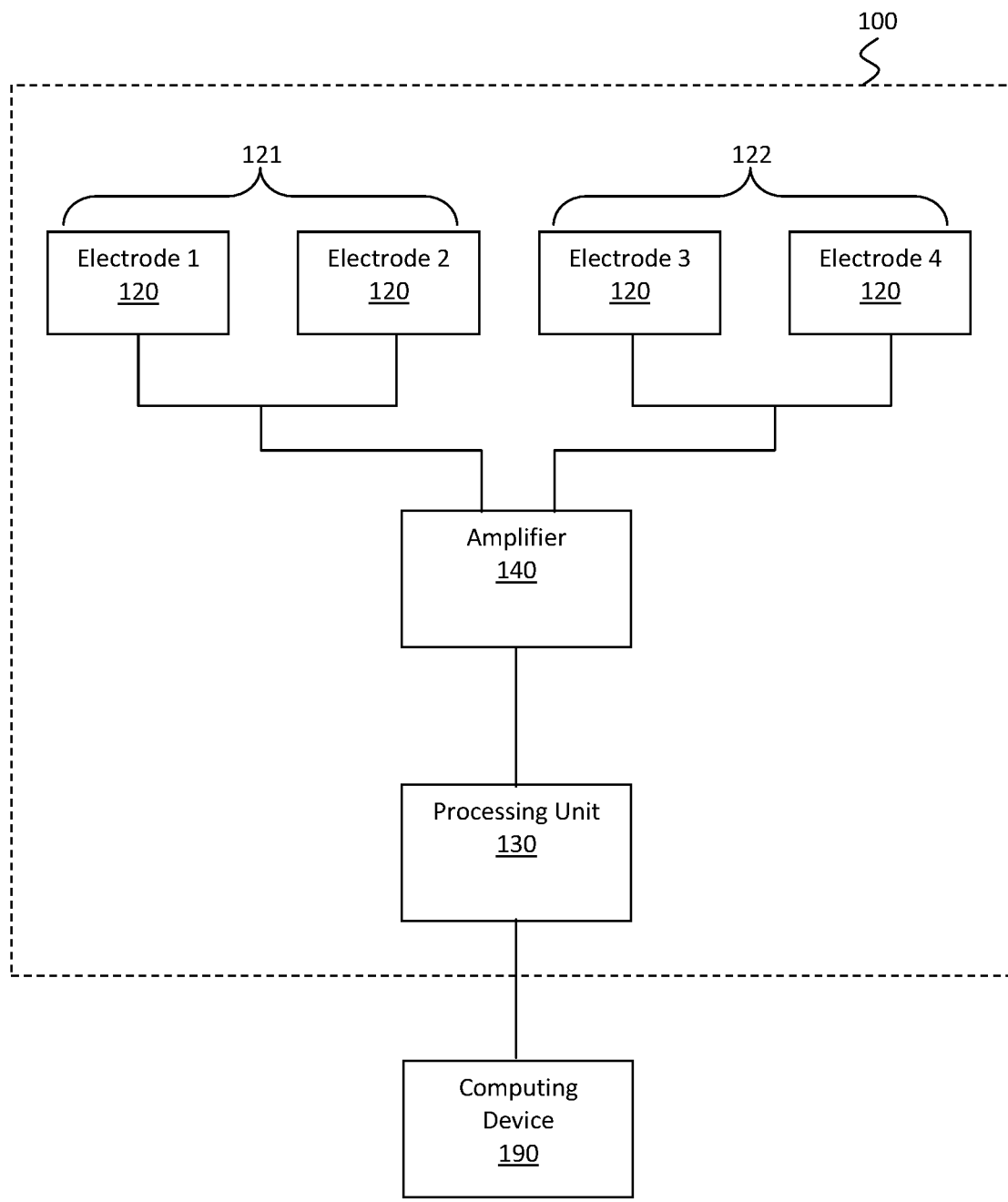
FIG. 2 shows a schematic view of electrical components of the electrode device of FIGS. 1a and 1b.

A schematic view of the electrical components of the electrode device 100 is provided in FIG. 2. The amplifier 140, whether integrated with or separate from the processing unit 130, may comprise a battery and may amplify electrical signals sent between the electrodes 120 and the processing unit 130. The processing unit 130 may comprise a transceiver, an analogue to digital converter, and a processor to process data relating to electrical signals received from or transmitted to the electrodes 120. The processing unit 130 may include a memory to store the processed data. The processing unit 130 may be similar to a processing unit of a type commonly used with cochlear implants although other configurations are possible. The amplifier 140, e.g. when it is in line with the electrodes 120, may be made a medical grade titanium with ceramic feed through assemblies, for example.

The data processed and stored by the processing unit 130 may be raw EEG data, for example. The EEG data may be transmitted wirelessly, or via a wire, to an external computing device 190 for analysing the data. The computing device 190 may analyse raw EEG signals to determine if a target event has occurred. Data regarding the event may be generated by the computing device 190 on the basis of the analysis. In one example, the computing device 190 may analyse brain activity signals to determine if a target event such as an epileptic event has occurred and data regarding the epileptic event may be generated by the computing device 190 on the basis of the analysis.

By carrying out data analysis externally to the electrode device 100, using the computing device 190, for example, there may be a reduction in power consumption within the electrode device 100, enabling the electrode device 100 to retain a smaller geometrical form. Moreover, the computing device 190 may have significantly higher processing power than would be possible with any processor included in the electrode device 100. The computing device 190 may run software that continuously records electrical data received from the electrode device 100.

The processing unit 130 and/or computing device 190 can comprise a digital signal processor (DSP) and/or other components and/or software modules to carry out signal processing. In general, it will be recognised that any processer that is used may comprise a number of control or processing modules for controlling one or more features of the present disclosure and may also include one or more storage elements, for storing desired data, e.g., raw or processed EEG data. The modules and storage elements can be implemented using one or more processing devices and one or more data storage units, which modules and/or storage devices may be at one location or distributed across multiple locations and interconnected by one or more communication links. Processing devices used in conjunction with the electrode device may include microprocessors, desktop computers, laptop computers, tablets, smartphones, personal digital assistants and other types of devices, including devices manufactured specifically for the purpose of carrying out methods according to the present disclosure.

Further, the processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

Figure 3B:
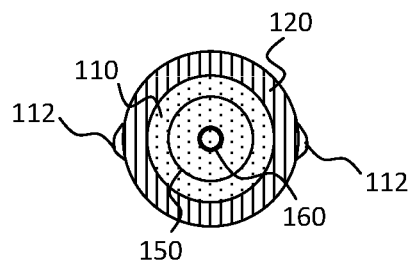
Figure 3C:
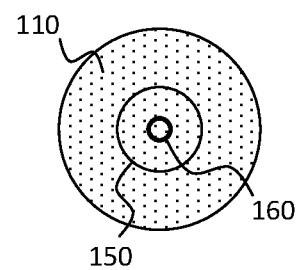

With reference to FIGS. 3b and 3c, which provide cross-sectional views along lines B-B and C-C in FIG. 3a, respectively, the implantable body 110 has a round, e.g., substantially circular or ovate, cross-sectional profile. Similarly, each of the electrodes 120 has a round, e.g., substantially circular or ovate, cross sectional profile. Each of the electrodes 120 extend circumferentially, completely around a portion of the implantable body 110. By configuring the implantable body 110 and electrodes 120 in this manner, the exact orientation of the implantable body 110 and electrodes 120, when implanted in a subject, is less critical. For example, the electrodes 120 may interact electrically with tissue in substantially any direction. In this regard, the electrodes 120 may be considered to have a 360 degree functionality. The round cross-sectional configuration can also provide for easier insertion of the implantable portions of the electrode device 100 to the target location and with less risk of damaging body tissue. For example, the implantable body 110 can be used with insertion cannulas or sleeves and may have no sharp edges that might otherwise cause trauma to tissue.

In this embodiment, the implantable body 110 is formed of an elastomeric material such as medical grade silicone. Each electrode 120 comprises an annular portion of conductive material that extends circumferentially around a portion of the implantable body 110. More specifically, each electrode 120 comprises a hollow cylinder of conductive material that extends circumferentially around a portion of the implantable body 110 and, in particular, a portion of the elastomeric material of the implantable body 110. The electrodes 120 may be considered 'ring' electrodes.

However, in alternative embodiments, electrodes may be provided that do not extend completely around the circumference of a portion of the elastomeric material of the implantable body. For example, with reference to FIGS. 16a to 16c, in one embodiment, one or more electrodes 410 are designed to extend part way around, and more particularly about three-quarters of the way around, the circumference of a portion of the elastomeric material of the implantable body 110'. Moreover, with reference to FIGS. 17a to 17c, in one embodiment, one or more electrodes 420 are designed to extend part way around, and more particularly about half of the way around, the circumference of a portion of the elastomeric material of the implantable body 110". In the embodiments of FIGS. 16a to 17c, the electrodes 410, 420 are part-cylinders of conductive material, a quarter or half circumferential section of the cylinder being absent. By having a quarter or a half of the circumference of the cylinder absent, or indeed anywhere between about a quarter and about a half of the cylinder absent, for example, the fabrication process for the electrode device may be simplified. It can allow elastomeric material and/or other features of the electrode device to be extended through the side of electrode without having to be fed through an end of the electrode for example.

Figure 4A:
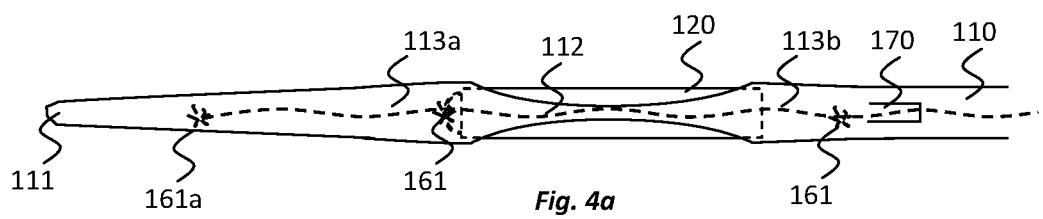
FIGS. 4a and 4b show top and side views, respectively of a distal end portion of the electrode device of FIGS. 1a and 1b.
Figure 4B:
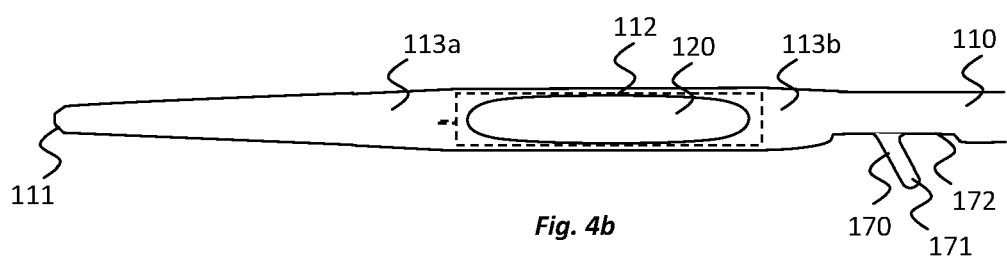

Referring back to the embodiment of FIGS. 1a and 1b, and with further reference to FIGS. 4a and 4b, to strengthen the engagement between the electrodes 120 and the implantable body 110, straps 112 are provided in this embodiment that extend across an outer surface of each electrode 120. In this embodiment, two straps 112 are located on substantially opposite sides of each electrode 120 in a direction perpendicular to the direction of elongation of the implantable body 110. The straps 112 are connected between sections 113a, 113b of the implantable body 110 that are located on opposite sides of the electrodes 120 in the direction of elongation of implantable body, which sections 113a, 113b are referred to hereinafter as side sections. The straps 112 can prevent the side sections 113a, 113b from pulling or breaking away from the electrodes 120 when the implantable body 110 is placed under tension and/or is bent. In this embodiment, the straps 112 are formed of the same elastomeric material as the side sections 113a, 113b. The straps 112 are integrally formed with the side sections 113a, 113b. From their connection points with the side sections 113a, 113b, the straps 112 decrease in width towards a central part of the each electrode 120, minimising the degree to which the straps 112 cover the surfaces of the electrodes 120 and ensuring that there remains a relatively large amount of electrode surface that is exposed around the circumference of the electrodes 120 to make electrical contact with adjacent body tissue. With reference to FIG. 3b, around a circumference of each electrode, at least 75% of the outer electrode surface, at least 80%, at least 85% or at least 90% of the outer electrode surface may be exposed for electrical contact with tissue, for example.

In alternative embodiments, a different number of straps 112 may be employed, e.g., one, three, four or more straps 112. Where a greater number straps 112 are employed, the width of each strap 112 may be reduced. The straps 112 may be distributed evenly around the circumference of each electrode 120 or distributed in an uneven manner. Nevertheless, in some embodiments, the straps 112 may be omitted, ensuring that all of the outer electrode surface is exposed for electrical contact with tissue, around a circumference of the electrode 120.

An embodiments in which straps have been omitted is illustrated in FIGS. 18a to 18c. In this embodiment, an electrode 430 is provided that has been modified to include portions of reduced diameter 431 at opposite ends of the electrode 430 in the direction of elongation of the electrode device. The reduced diameter is achieved by providing a reduced thickness to the wall of the cylinder that forms the electrode 430, although additionally or alternatively the reduced diameter portions may be formed through bending or shaping of conductive material forming the electrode or otherwise. As shown in FIG. 18c, the reduced diameter portions are configured to lie under, e.g. remain fully embedded in, the elastomeric material of the implantable body 110'''. Elastomeric material can extend both over the reduced diameter portions 431 and under the reduced diameter portions 431, trapping these portions of the electrodes within the implantable body and strengthening the engagement with the implantable body. Similar reduced diameter portions 411, 421 can be provided with electrodes that are formed as part-cylinders, e.g., as per the electrodes 410, 420 illustrated in FIGS. 16a to 17c.

As shown in FIG. 18b, at the reduced diameter portions 431, or indeed any other portions of the electrodes that are directly connected to the elastomeric material, one or more apertures 433, e.g. holes and/or slots, etc., may be provided. During manufacture, elastomeric material may flow through the apertures 433, locking the electrodes 430 to the implantable body. Similar apertures may be introduced to the electrodes of other embodiments, such as those illustrated in FIGS. 16 to 17c.

As indicated above, the implantable body 110 is formed of an elastomeric material such as silicone. The elastomeric material allows the implantable body 110 to bend, flex and stretch such that the implantable body 110 can readily contort as it is routed to a target implantation position and can readily conform to the shape of the body tissue at the target implantation position. The use of elastomeric material also ensures that any risk of trauma to the subject is reduced during implantation or during subsequent use.

In embodiments of the present disclosure the electrical connection 150 to the electrodes 120 comprises relatively fragile platinum wire conductive elements. With reference to FIGS. 3a to 3c, for example, to reduce the likelihood that the platinum wires will break or snap during bending, flexing and/or stretching of the implantable body 110, the electrical connection 150 is provided with wave-like shape and, more specifically, a helical shape in this embodiment, although other non-linear shapes may be used. The helical shape, for example, of the electrical connection 150 enables the electrical connection 150 to stretch, flex and bend in conjunction with the implantable body. Bending, flexing and/or stretching of the implantable body 110 typically occurs during implantation of the implantable body in a subject and upon any removal of the implantable body 110 from the subject after use.

As indicated above, a reinforcement device 160 is also provided in the electrode device 100, which reinforcement device 160 extends through the implantable body 110 and is provided to limit the degree by which the length of the implantable body 110 can extend under tension. The reinforcement device 160 can take the bulk of the strain placed on the electrode device 110 when the electrode device 100 is placed under tension. The reinforcement device 160 is provided in this embodiment by a fibre (e.g., strand, filament, cord or string) of material that is flexible and which has a high tensile strength. In particular, a fibre of ultra-high-molecular-weight polyethylene (UHMwPE), e.g., Dyneema™, is provided as the reinforcement device 160 in the present embodiment. The reinforcement device 160 extends through the implantable body 110 in the length direction of the implantable body 110 and is generally directly encased by the elastomeric material of the implantable body 110.

The reinforcement device 160 may comprise a variety of different materials in addition to or as an alternative to UHMwPE. The reinforcement device may comprise other plastics and/or non-conductive material such as a poly-paraphenylene terephthalamide, e.g., Kevlar™. In some embodiments, a metal fibre or surgical steel may be used.

Similar to the electrical connection 150, the reinforcement device 160 also has a wave-like shape and, more specifically, a helical shape in this embodiment, although other non-linear shapes may be used. The helical shape of the reinforcement device 160 is different from the helical shape of the electrical connection 150. For example, as evident from FIGS. 3a to 3c, the helical shape of the reinforcement device 160 has a smaller diameter than the helical shape of the electrical connection 150. Moreover, the helical shape of the reinforcement device 160 has a greater pitch than the helical shape of the electrical connection 150.

Figure 5A:
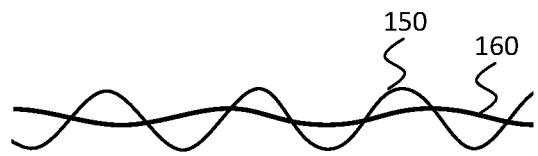
FIGS. 5a and 5b show representations of a reinforcement device, and an electrical connection, of the electrode device of FIGS. 1a and 1b, before and after a tensile force is applied to the reinforcement device and the electrical connection.
Figure 5B:
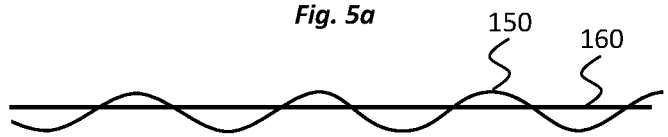

When the implantable body 110 is placed under tension, the elastomeric material of the implantable body will stretch, which in turns causes straightening of the helical shapes of both the electrical connection 150 and the reinforcement device 160, as evident from a comparison of FIGS. 5a and 5b. As the electrical connection 150 and the reinforcement device straighten 160, their lengths can be considered to increase in the direction of elongation of the implantable body 110. Thus, the lengths of each of the electrical connection 150 and the reinforcement device 160, in the direction of elongation of the implantable body 110, are extendible when the implantable body 110 is placed under tension.

For each of the electrical connection 150 and the reinforcement device 160, a theoretical maximum length of extension in the direction of elongation of the implantable body is reached when its helical shape (or any other non-linear shape that may be employed) is substantially completely straightened. However, due to the differences in the helical shapes of the electrical connection 150 and the reinforcement device 160, the maximum length of extension of the reinforcement device 160 is shorter than the maximum length of extension of the electrical connection 150. Therefore, when the implantable body 110 is placed under tension, the reinforcement device 160 will reach its maximum length of extension before the electrical connection 150 reaches its maximum length of extension (again as illustrated in FIGS. 5a and 5b). Indeed, the reinforcement device 160 can make it substantially impossible for the electrical connection 150 to reach its maximum length of extension. Since the electrical connection 150 can be relatively fragile and prone to breaking, particularly when placed under tension, and particularly when it reaches a maximum length of extension, the reinforcement device 160 can reduce the likelihood that the electrical connection 150 will be damaged when the implantable body 110 is placed under tension. In contrast to the electrical connection 150, when the reinforcement device 160 reaches its maximum length of extension, its high tensile strength allows it to bear a significant amount of strain placed on the electrode device 100, preventing damage to the electrical connection 150 and other components of the electrode device 100.

In consideration of other components of the electrode device 100 that are protected from damage by the reinforcement device 160, it is notable that the implantable body 110 can be prone to damage or breakage when it is placed under tension. The elastomeric material of the implantable body 110 has a theoretical maximum length of extension in its direction of elongation when placed under tension, the maximum length of extension being the point at which the elastomeric material reaches its elastic limit. In this embodiment, the maximum length of extension of the reinforcement device 160 is also shorter than the maximum length of extension of the implantable body 110. Thus, when the implantable body 110 is placed under tension, the reinforcement device 160 will reach its maximum length of extension before the implantable body 110 reaches its maximum length of extension. Indeed, the reinforcement device 160 can make it substantially impossible for the implantable body 110 to reach its maximum length of extension. Since elastomeric material of the implantable body 110 can be relatively fragile and prone to breaking, particularly when placed under tension, and particularly when it reaches its elastic limit, the reinforcement device 160 can reduce the likelihood that the implantable body 110 will be damaged when it is placed under tension.

In this embodiment, the helical shapes of the reinforcement device 160 and the electrical connection 150 are provided in a concentric arrangement. Due to its smaller diameter, the reinforcement device 160 can locate radially inside of the electrical connection 150. In view of this positioning, the reinforcement device provides a form of strengthening core to the implantable body 110. The concentric arrangement can provide for increased strength and robustness while offering optimal surgical handling properties, with relatively low distortion of the implantable body 110 when placed under tension.

As indicated, the reinforcement device 160 is directly encased by the elastomeric material of the implantable body 110. The helically-shaped reinforcement device 160 therefore avoids contact with material other than the elastomeric material in this embodiment. The helically shaped reinforcement device is not entwined or intertwined with other strands or fibres, for example (e.g., as opposed to strands of a rope), ensuring that there is a substantial amount of give possible in relation to its helical shape. The helical shape can move to a straightened configuration under tension as a result, for example.

The arrangement of the reinforcement device 160 is such that, when the implantable body 110 is placed under tension, the length of the reinforcement device 160 is extendible by about 20% of its length when the implantable body 110 is not under tension. Nevertheless, in embodiments of the present disclosure, a reinforcement device 160 may be used that is extendible by at least 5%, at least 10%, at least 15%, at least 20% or at least 25% or otherwise, of the length of the reinforcement device when the implantable body is not under tension. The maximum length of extension of the reinforcement device in the direction of elongation of the implantable body may be about 5%, about 10%, about 15%, about 20% or about 25% or otherwise of its length when the implantable body is not under tension.

Figure 6:
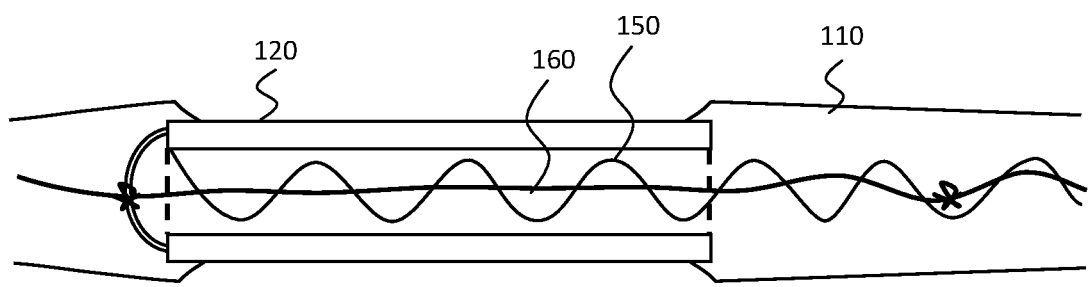
FIG. 6 shows a cross-sectional view of a portion of an electrode device according to an alternative embodiment of the present disclosure.

As represented in FIG. 3a, the reinforcement device 160 has a relatively uniform helical configuration along its length. However, in some embodiments, the shape of the reinforcement device can be varied along its length. For example, as illustrated in FIG. 6, the reinforcement device can be straighter (e.g., by having a helical shape with smaller radius and/or greater pitch) adjacent the electrodes 120 in comparison to at other portions of the implantable body 110. By providing this variation in the shape of the reinforcement device, stretching of the implantable body 110 may be reduced adjacent the electrodes 120, where there could otherwise be a greater risk of the electrodes 120 dislocating from the implantable body 110. This enhanced strain relief adjacent the electrodes 120 can be provided while still maintaining the ability of the reinforcement device 160, and therefore implantable body 110, to stretch to a desirable degree at other portions of the implantable body 110.

As indicated, the electrical connection 150 in this embodiment comprises relatively fragile platinum wire conductive elements. At least 4 platinum wires are provided in the electrical connection 150 to each connect to a respective one of the four electrodes 120. The wires are twisted together and electrically insulated from each other. Connection of a platinum wire of the electrical connection 150 to the most distal of the electrodes is illustrated in FIG. 3a. As can be seen, the wire is connected to an inner surface 1210 of the electrode 120, adjacent a distal end of the electrode 120, albeit other connection arrangements can be used.

The reinforcement device 160 extends through the hollow centre of each of the electrodes 120. The reinforcement device 160 extends at least from the distal most electrode 120, and optionally from a region adjacent the distal tip 111 of the implantable body 110, to a position adjacent the amplifier 140. In some embodiments, the reinforcement device 160 may also extend between the amplifier 140 and the processing unit 130. In some embodiments, the reinforcement device 160 may extend from the distal tip 111 and/or the distal most electrode 120 of the implantable body 110 to the processing unit 130.

To prevent the reinforcement device 160 from slipping within or tearing from the elastomeric material of the implantable body 110, a series of knots 161 are formed in the reinforcement device 160 along the length of the reinforcement device 160. For example, with reference to FIG. 4a, a knot 161a can be formed at least at the distal end of the reinforcement device 160, adjacent the distal tip 111 of the implantable body 110, and/or knots 161 can be formed adjacent one or both sides of each electrode 120. The knots may alone provide resistance to movement of the reinforcement device 160 relative to the elastic material of the implantable body and/or may be used to fix (tie) the reinforcement device 160 to other features of the device 100.

In the present embodiment for example, as illustrated in FIG. 3a, the reinforcement device 160 is fixed, via a knot 161b, to each electrode 120. To enable the reinforcement device 160 to be fixed to the electrode 120, the electrode 120 comprises an extension portion 1220 around which knots 161 of the reinforcement device 160 can be tied. As shown in FIG. 3a, the extension portion 1220 can include a loop or arm of material that extends across an open end of the hollow cylinder forming the electrode 120. Another example of a loop or arm, providing an extension portion 432 of an electrode 430 to which a reinforcement device 1600 is tied using a knot 1601, or is otherwise connected, is provided in the embodiment illustrated in FIGS. 18a to 18c. In a further alternative embodiment, and as illustrated in FIGS. 19a to 19c, a conduit or eye 442 may be located within an electrode 440, e.g. within the hollow cylinder of the electrode 440, to which a the reinforcement device 1610 is tied, or is otherwise connected. A knot 1611 may be formed on one or both sides of the conduit or eye 442 to prevent relative axial movement between the reinforcement device 1610 and the electrode 440. The extension portion 432 or the conduit or eye 442 can be utilised with other embodiments of the electrodes, e.g. including those having a part-cylindrical shape as illustrated in FIGS. 16a to 17c, for example.

With reference to FIGS. 1a, 1b, 4a, 4b, and 7a to 7c, the electrode device 100 comprises at least one anchor 170, and in this embodiment of plurality of anchors 170. The plurality of anchors 170 are positioned along a length of the implantable body 110, each adjacent a respective one of the electrodes 120. Each anchor 170 is configured to project radially outwardly from the implantable body 110 and specifically, in this embodiment, at an angle towards a proximal end of the implantable body 110. Each anchor 170 is in the form of a flattened appendage or fin with a rounded tip 171. The anchors 170 are designed to provide stabilisation to the electrode device 100 when it is in the implantation position. When implanted, a tissue capsule can form around each anchor 170, securing the anchor 170 and therefore the implantable body 110 into place. In this embodiment, the anchors 170 are between about 0.5 mm and 2 mm in length, e.g., about 1 mm or 1.5 mm in length.

So that the anchors 170 do not impede implantation of the electrode device 100, or removal of the electrode device 100 after use, each anchor 170 is compressible. The anchors 170 are compressible (e.g., foldable) to reduce the degree by which the anchors 170 projects radially outwardly from the implantable body 110. To further reduce the degree by which the anchors 170 project radially outwardly from the implantable body 110 when compressed, a recess 172 is provided in a surface of the implantable body 110 adjacent each anchor 170. The anchor is compressible into the recess 172. In this embodiment, the anchors 170 project from a bottom surface of the respective recess 172 and the recess extends on both proximal and distal sides of the anchor 170. Accordingly, the anchors 170 can be compressed into the respective recesses in either a proximal or distal direction, as illustrated in FIGS. 7b and 7c. This has the advantage of allowing the anchors 170 to automatically move into a storage position in the recess 172 when pulled across a tissue surface or a surface of a implantation tool such as delivery device, in either of a proximal and a distal direction.

The electrode device 100 of the present embodiment is configured for use in monitoring electrical activity in the brain and particularly for monitoring electrical activity relating to epileptic events in the brain. The electrode device 100 is configured to be implanted at least partially in a subgaleal space between the scalp and the cranium. At least the electrodes 120 and adjacent portions of the implantable body 110 are located in the subgaleal space.

Figure 8:
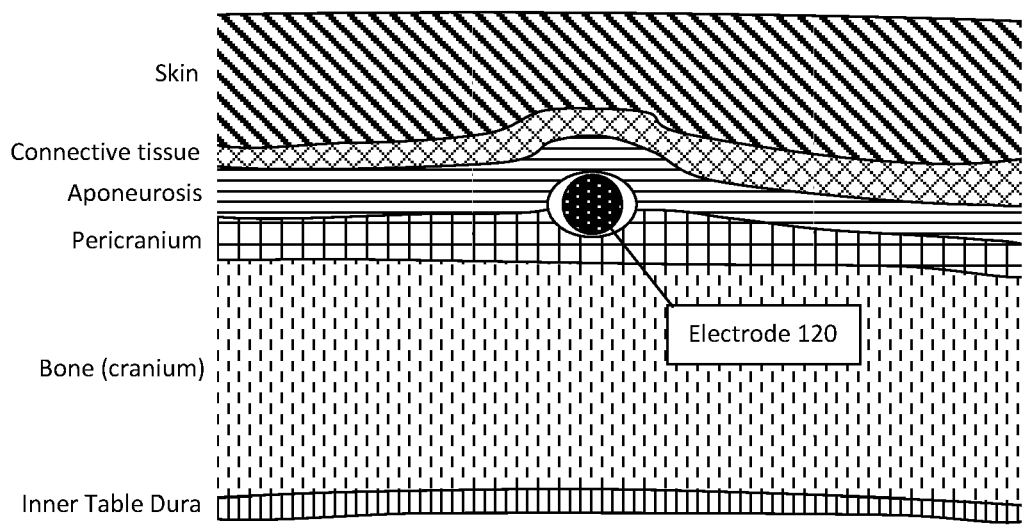
FIG. 8 illustrates an implantation location of electrodes of an electrode device according to an embodiment of the present disclosure.
Figure 9:
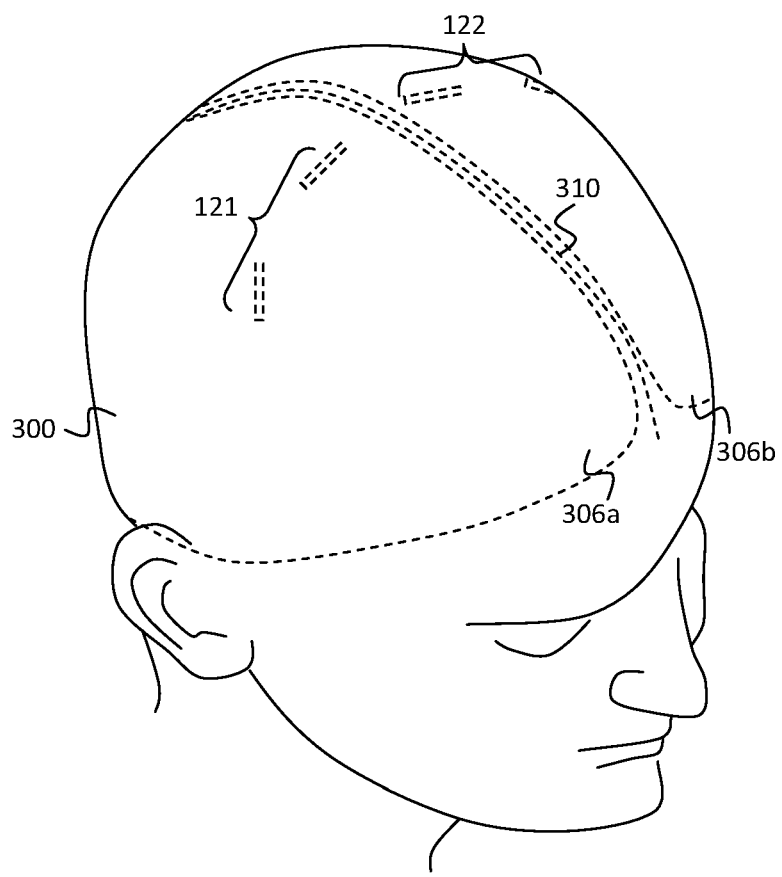
FIG. 9 further illustrates an implantation location of electrodes of an electrode device according to an embodiment of the present disclosure.

An illustration of the implantation location of the electrodes 120 is provided in FIG. 8. As can be seen, the electrodes 120 locate in particular in a pocket between the galea aponeurotica and the pericranium. Referring also to FIG. 9, when implanted, the first and second electrode pairs 121, 122 are located on respective sides of the midline 310 of the head 300 of the subject in a substantially symmetrical arrangement. The first and second electrode pairs 121, 122 therefore locate over the right and left hemispheres 306a, 306b of the brain, respectively. For example, the first electrode pair 121 can be used to monitor electrical activity at right hemisphere 306a of the brain and the second electrode pair 121 can be used to monitor electrical activity at the left hemisphere of the brain 306b, or vice-versa. Independent electrical activity data may be recorded for each of the right and left hemispheres, e.g., for diagnostic purposes, To position the electrodes pairs 121, 122 over the right and left hemispheres 306a, 306b of the brain, the implantable body 110 of the electrode device is implanted in a medial-lateral direction over the cranium of the subject's head 180. The electrode pairs 121, 122 are positioned away from the subject's eyes and chewing muscles to avoid introduction of signal artifacts from these locations.

A method of implanting the electrode device 100 according to an embodiment of the present disclosure is described further below with reference to FIGS. 12a to 12d. The method employs a delivery device 200, as illustrated in FIGS. 10a, 10b and 11. The delivery device 200 can create a subgaleal pocket in which the electrode device 100 locates, and can assist with channelling of the electrode device 100 to this implantation location, i.e. into the subgaleal pocket. Slight modifications may be made to the method and associated delivery device when the electrode device is for use at other locations of the human or animal body.

Figure 12A:
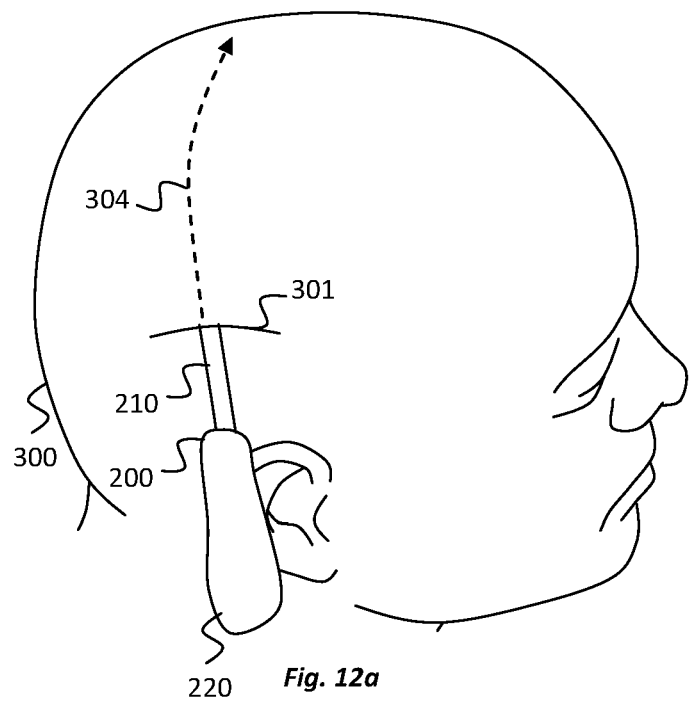
FIGS. 12a and 12b illustrate steps in a method of implanting an electrode device according to an embodiment of the present disclosure.
Figure 12B:
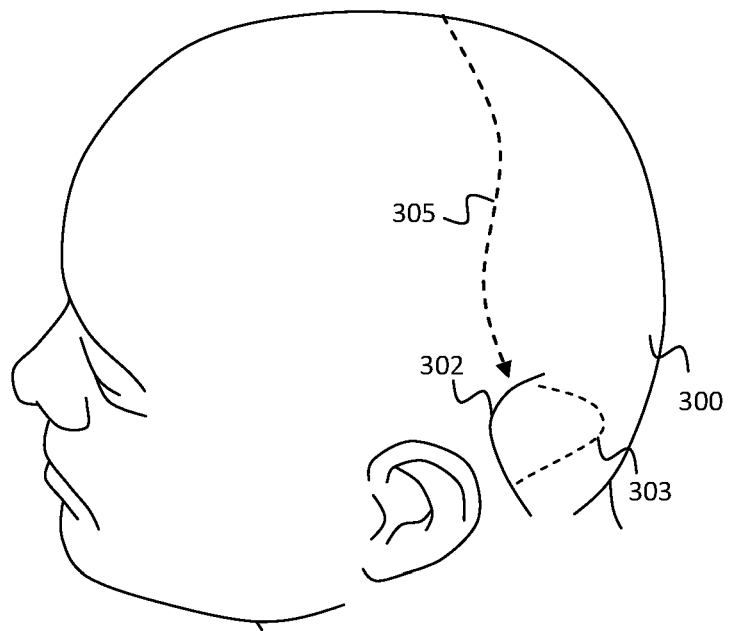

The delivery device 200, which may also be considered a "trocar", for example, comprises a cannula 210 that has a length sufficient to reach over the subject's skull between a first incision 301 that is located posteriorly of the temple on one side of the subject's head and a second incision 302 that is located posteriorly of the ear on the other side of the subject's head. The locations of the first and second incisions 301, 302 are illustrated in FIGS. 12a and 12b, respectively, and the purpose of the incisions 301, 302 is described in more detail below.

At a proximal end of the cannula 210, the delivery device 200 comprises a handle 220 that can be gripped by the surgeon to manipulate movement of the cannula 210 through the first incision 301 and over the subject's skull. The handle 220 is ergonomically shaped for comfort and is formed from two hollow shells that are fixed together, e.g., using screws. The handle design may be particularly suited for forming using 3D printing.

The delivery device 200 also comprises a releasable inner member, and in this embodiment an inner filament 230, that extends through a central channel of the cannula 210 and has a distal tip 231 that is exposed at a distal end opening 211 of the cannula 210. The distal tip 231 of the filament 200 is pointed to provide a leading end of the delivery device 200 that can navigate or tunnel through, and open up a pocket between, tissue layers. The distal tip 231 is located distally of the distal end opening 211 of the cannula 210. The filament 230 extends from the distal end opening 211 of the cannula 210 to a location inside the handle 220.

The cannula 210 comprises flexible material that is pre-curved in an S-shape. The pre-curved shape is designed to assist in tunnelling of the cannula 210 almost 150 to 180 degrees around the skull, while avoiding the need to make more than two incisions and to use multiple tunnelling trajectories, for example. The curvature of the cannula 210 may approximately match a curvature of the skull, for example. The cannula 210 has different flexibility properties along its length. In this embodiment, the different flexibility is provided by modifying the thicknesses of the walls of the cannula 210. A distal portion 210a of the cannula 210 is more flexible than a proximal portion 210b. The flexibility of the cannula 210 increases towards its distal end opening 211, e.g., progressively or discretely. The changing flexibility again assists in tunnelling of the cannula 210 around the skull. For example, the more-flexible distal portion 210a can allow a surgeon to manually bend that portion 210a during tunnelling and can reduce this risk of any trauma that may be caused to body tissue as it progresses between tissue layers. Moreover, the less-flexible proximal portion 210b can provide greater stiffness to the cannula to withstand forces applied to the cannula as it is pushed into position; the proximal portion 201b may be much less likely to buckle due to its relatively high wall thickness, for example.

The distal tip 231 of the filament 230 is asymmetrically shaped, with a flatter surface at the side of the delivery device 200 that is configured to face the skull and a more angled surface at the side of the delivery device 200 that is configured to face away from the skull. The use of the asymmetrically shaped tip 231 can also assist with tunnelling of the cannula 210 around the skull and can again reduce the risk of any trauma that may be caused to body tissue as it progresses between tissue layers.

The filament 230 is releasably locked into position in the cannula 210 using a locking mechanism 240 at the handle 220 of the delivery device 200. The locking mechanism includes an abutment 241 configured to engage one side of the filament 230 and a cam 242 configured to engage a second, opposite side of the filament 230. The cam 242 is rotatable in a first direction to increase an engagement force applied to the filament 230 between the cam 242 and the abutment 241, and is rotatable in a second, opposite direction to release the engagement force applied to the filament 230 between the cam 242 and the abutment 241. The locking mechanism 240 also includes a button 243 operable by a surgeon at a surface of the handle 220. The button 243 is connected to the abutment 241 and slidable in a distal-proximal direction of the delivery device 200 to cause rotation of the cam 242 in the first and second directions, as desired to lock and release locking of the filament 230. In this embodiment, the button 243 is slidable in a proximal direction to lock the filament 230 and in a distal direction to release locking of the filament 230. The locking mechanism is designed such that, on releasing of the locking of the filament 230, the distal dip 231 of the filament is automatically moved forward (distally), away from the distal end 211 opening of the cannula 210. For example, the distal tip 231 may be moved about 5 mm forward. By moving forward, the distal tip 231 of the filament 230 may be more easily engaged by the surgeon for removal from the cannula 210.

Referring to FIGS. 12a and 12b, to implant the electrode device 100, the surgeon uses a scalpel or other cutting device to create the first and second incisions 301, 302 on the opposite sides of the subject's head 300. The incisions 301, 302 are made at least as deep as pericranial layer (pericranium) of the scalp that is illustrated in FIG. 8. Adjacent the second incision 302, the surgeon also opens a posterior pocket 303 in the scalp for receiving at least the processing unit 140 of the electrode device 100 when the electrode device 100 is fully implanted. The pocket 303 may be formed using a blunt blade or other suitable tool.

Referring to FIG. 12a, the leading end 231 of the delivery device 200 is introduced through the first incision 301 and into the subgaleal space. The delivery device 200 is pushed through the subgaleal space, in a direction indicated by the arrow 304, over the top of the subject's skull, generally in a medial-lateral direction. Referring to FIG. 12b, the delivery device 200 is pushed such that it continues to travel, in a direction indicated by the arrow 305 until it reaches the second incision 302 on the opposite side of the subject's head 300.

Figure 13A:
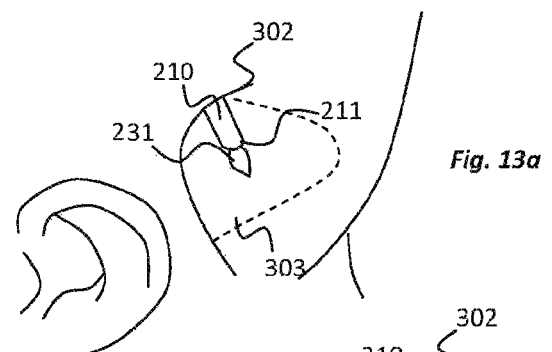
FIGS. 13a to 13d further illustrate steps in a method of implanting an electrode device according to an embodiment of the present disclosure.
Figure 13B:
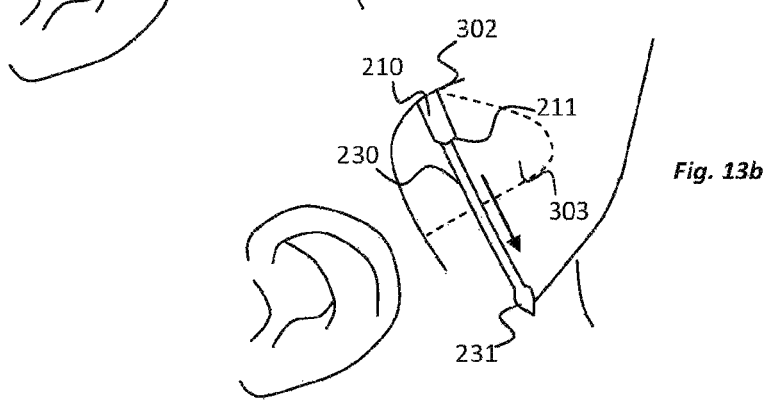

The delivery device 200 is ultimately moved to a location where its leading end, and more specifically the pointed distal tip 231 of the filament 230, along with the distal end opening 211 of the cannula 210, is exposed from the second incision 302, as illustrated in FIG. 13a. After releasing of the filament locking mechanism 240, by sliding of the button 243 on the handle 220 of the delivery device 200, the surgeon grips the distal tip 231 of the filament 230, using his/her fingers or a gripping tool, and pulls the filament 230 completely out of the cannula 210, as illustrated in FIG. 13b. This leaves the central channel of the cannula 210 empty and the distal end opening 211 of the cannula 210 uncovered.

Figure 13C:
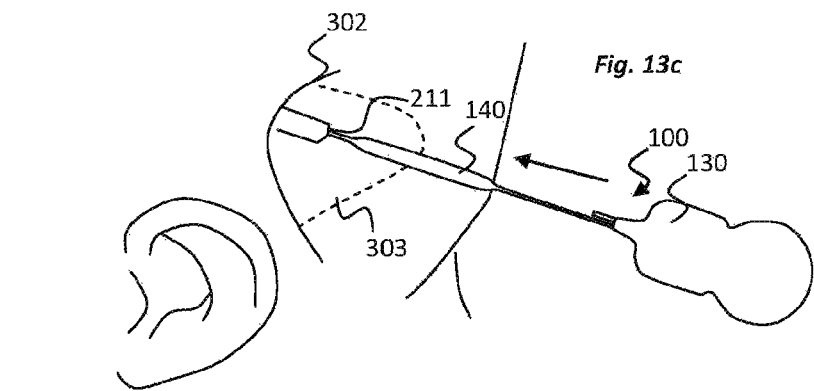

Referring to FIG. 13c, the distal tip 111 of the electrode device 100 is then inserted through the distal end opening 211 of the cannula 210 and into the central channel of the cannula 210. During this process, the cannula 210 remains substantially stationary with respect to the subject's skull, while the electrode device 100 is fed along the central channel of the cannula 210 and therefore over the subject's skull. As it is fed along the central channel, the plurality of anchors 170 that are positioned along a length of the implantable body 110 of the electrode device 100 are forced into a compressed (folded) state, generally as indicated in FIG. 7b, ensuring that the anchors 170 do not obstruct the insertion process.

Figure 13D:
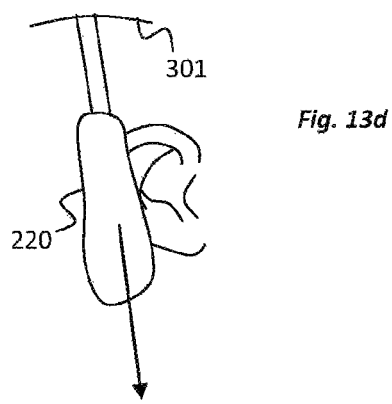
Figure 14:
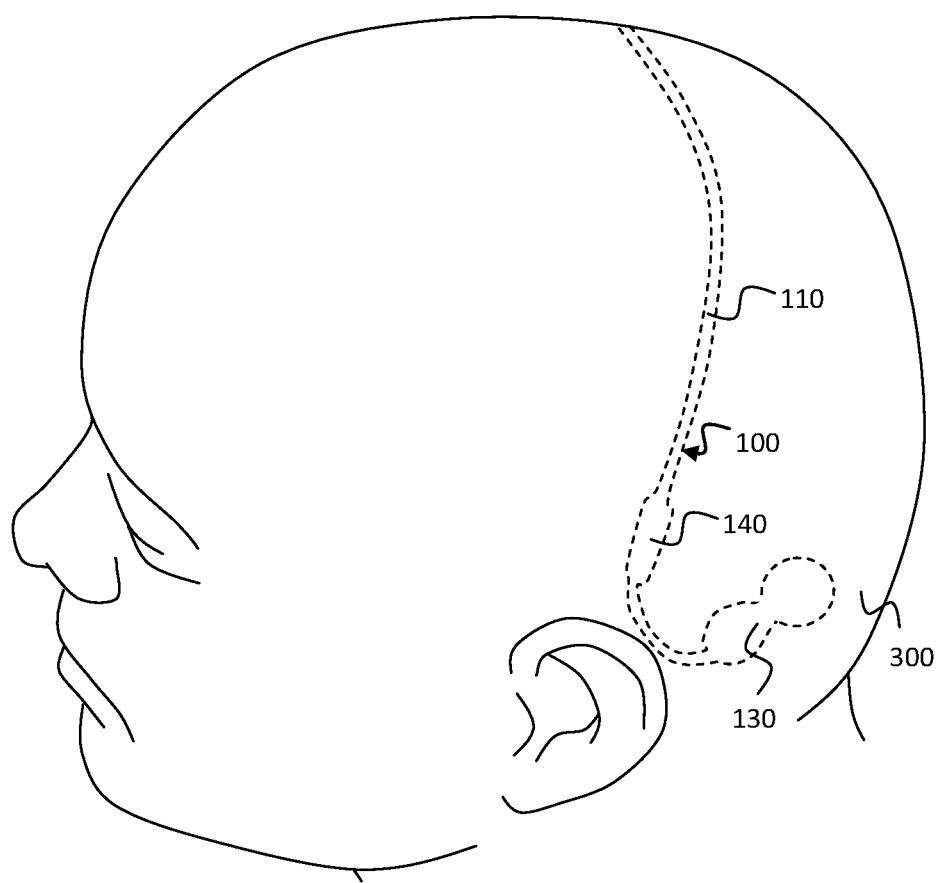
FIG. 14 illustrates an implantation location of an electrode device according to an embodiment of the present disclosure.

All of the electrode device 100 is fed into the cannula 210, except primarily for the processing unit 130, which is too large to extend through the cannula 210. At the end of the insertion process, when the processing unit 130 of the electrode device 100 reaches a position adjacent the distal end opening 211 of the cannula 210, the processing unit 130 is tucked into the posterior pocket 303. The delivery device 200 can then be fully withdrawn from the first incision 301 as illustrated in FIG. 13d. During the withdrawal process, the electrode device 100 remains substantially stationary with respect to the subject's skull, at the desired implantation location, with the anchors returning to their radially-projected configurations as illustrated in FIG. 7a. The first and second incisions 301, 302 can then be closed, e.g., by suturing, leaving the electrode device 100 implanted under the scalp in a position generally as illustrated in FIG. 14.

After use, to remove the electrode device 100, the surgeon can re-open the second incision 302, or make a further incision adjacent the second incision 302. The processing unit 140 can be removed from the pocket 303 and then the implantable body 110 pulled out of the incision. As it is pulled out of the incision, the implantable body 100 may stretch and flex, but the degree to which stretching takes place can be controlled by the reinforcement device 160 in a manner as discussed above, preventing damage to the electrode device 100. As it is pulled out of the incision, the plurality of anchors 170 that are positioned along a length of the implantable body 110 are again forced into a compressed (folded) state, generally as indicated in FIG. 7c, ensuring that the anchors 170 do not obstruct the removal process.

It will be appreciated by persons skilled in the art that numerous variations and/or modifications may be made to the above-described embodiments, without departing from the broad general scope of the present disclosure. For example, the electrode devices according to embodiments of the present disclosure may be adapted for use in monitoring and/or stimulating brain activity that is not related to epileptic events and/or does not rely on the obtaining of EEG signals. The present embodiments are, therefore, to be considered in all respects as illustrative and not restrictive.

The invention claimed is:

1. An electrode device comprising:
an elongate, implantable, one-piece body of elastomeric material,
a plurality of electrodes positioned on, and spaced apart along, a length of the one-piece body;
a helically-shaped electrical connection comprising one or more conductive elements extending through the one-piece body and electrically connecting to the plurality of electrodes; and
a reinforcement device extending through the one-piece body and located radially inside of the helical-shape of the electrical connection;
wherein the reinforcement device has a helical shape or a wave shape;
wherein a portion of the one-piece body is located between the reinforcement device and the electrical connection;
wherein the length of the one-piece body is extendible by placing the one-piece body under tension, the reinforcement device limiting the degree by which the length of the one-piece body can extend under tension.

2. The electrode device of claim 1, wherein, in the direction of elongation of the one-piece body, the length of the reinforcement device is extendible when the one-piece body is placed under tension.

3. The electrode device of claim 2, wherein, in the direction of elongation of the one-piece body, when the one-piece body is placed under tension, the reinforcement device has a maximum length of extension and the electrical connection has a maximum length of extension, the maximum length of extension of the reinforcement device being shorter than a maximum length of extension of the electrical connection.

4. The electrode device of claim 1, wherein, in the direction of elongation of the one-piece body, when the one-piece body is placed under tension, portions of the reinforcement device that are adjacent the plurality of electrodes are configured to extend less than portions of the reinforcement device that are spaced further away from the plurality of electrodes.

5. The electrode device of claim 1, wherein placing the one-piece body under tension causes straightening of the helical or wave shape of the reinforcement device and extending of the length of the reinforcement device.

6. The electrode device of claim 1, wherein the reinforcement device is straighter at the portions adjacent the electrodes than at the portions spaced from the plurality of electrodes.

7. The electrode device of claim 1, wherein the reinforcement device is configured to reach a maximum length of extension when the helical or wave shape of the reinforcement device is completely straightened.

8. The electrode device of claim 1, wherein the helical shapes of the reinforcement device and the electrical connection are concentric.

9. The electrode device of claim 1, wherein the reinforcement device is a fiber.

10. The electrode device of claim 9, wherein the outer surface of the fiber is directly encased by the elastomeric material of the one-piece body.

11. The electrode device of claim 1, wherein the reinforcement device is tied to at least one of the plurality of electrodes.

12. The electrode device of claim 1, wherein at least one of the plurality of electrodes comprises an annular portion of conductive material that extends circumferentially around a portion of the one-piece body.

13. The electrode device of claim 12, wherein the reinforcement device extends through the at least one of the plurality of electrodes.

14. The electrode device of claim 1, comprising at least one anchor positioned along a length of the one-piece body, wherein the at least one anchor projects radially outwardly from the one-piece body and at an angle towards a proximal end of the one-piece body.

15. The electrode device of claim 14, wherein a recess is provided in a surface of the one-piece body adjacent the at least one anchor, the at least one anchor being compressible into the recess.

16. The electrode device of claim 1, wherein at least one of the plurality of electrodes comprises a first pair of electrodes adapted to locate over one of the right and left hemispheres of a brain, and a second pair of electrodes adapted to locate over the other of the right and left hemispheres of the brain.

17. The electrode device of claim 1, wherein the electrode device is for monitoring brain activity signals.

18. The electrode device of claim 1, wherein at least the one-piece body of the electrode device is configured for implanting between the scalp and cranium of a subject.

19. The electrode device of claim 1, wherein the reinforcement device is a non-electrically conducting element of the electrode device.

20. The electrode device of claim 12, wherein the reinforcement device extends through the annular portion of the at least one of the plurality of electrodes and a portion of the reinforcement device that extends through the annular portion of the at least one of the plurality of electrodes is straighter than one or more adjacent portions of the reinforcement device that do not extend through the annular portion of the at least one of the plurality of electrodes.

* * * * *